United States Patent [19]

Bowden et al.

[11] Patent Number: 5,760,269
[45] Date of Patent: Jun. 2, 1998

[54] 4,4,4-TRICHLOROBUTYL METHANESULFONATE

[75] Inventors: Martin Charles Bowden, Brighouse; Trevor Robert Perrior, Finchampstead, both of United Kingdom

[73] Assignee: Zeneca Limited, London, England

[21] Appl. No.: 761,251

[22] Filed: Dec. 6, 1996

[30] Foreign Application Priority Data

Dec. 11, 1995 [GB] United Kingdom ............... 9525260
Jan. 5, 1996 [GB] United Kingdom ............... 9600162

[51] Int. Cl.$^6$ .................... C07C 303/30; C07C 309/66
[52] U.S. Cl. .................... 558/54; 568/56; 568/844
[58] Field of Search ................ 558/54; 568/56, 568/844

[56] References Cited

U.S. PATENT DOCUMENTS 4,009,191   2/1977   Baker ........................... 260/456

FOREIGN PATENT DOCUMENTS 1 243 677   7/1967   Germany.
2820/69     2/1969   Japan.
WO94/22815  10/1994  WIPO.
WO95/04727  2/1995   WIPO.

OTHER PUBLICATIONS

*Macromolecules* 1991, 24, 2475–2484—"Synthesis of Chlorinated Telechelic Oligomers. 2. Telomerization of Allyl Acetate with Functional Telogens"—B.Ameduri, B. Boutevin.

*J. Chem. Soc. Chem. Commun.*—1994, "Ring Opening Alkylation of Cyclic Ether with a–Halogenoalkyllithiums in the Presence of Boron Trifluoride–Diethyl Ether"—T. Imai, S. Nishida, T. Tsuji, No. 20, pp. 2353–2354.

Primary Examiner—Robert W. Ransuer
Assistant Examiner—Laura L. Stockton
Attorney, Agent, or Firm—Joel G. Ackerman

[57] ABSTRACT

The invention provides the novel compound 4,4,4-trichlorobutyl methanesufonate, useful as an intermediate in the production of certain agricultural pesticides, and a process for its manufacture.

7 Claims, No Drawings

4,4,4-TRICHLOROBUTYL METHANESULFONATE

The present invention relates to 4,4,4-trichlorobutyl methanesulfonate and processes for the its preparation and use as an intermediate particularly, but not exclusively, having application in the preparation of agricultural pesticides.

It has been found that compounds containing a 4,4,4-trichlorobutyl function are useful as intermediates in the preparation of compounds having applicability as agricultural pesticides. Examples of such intermediates include compounds such as 4,4,4-trichlorobutan-1-ol and 1,4,4,4-tetrachlorobutane.

The preparation of such compounds from 4,4,4-trichlorobutyl acetate has been proposed in a process involving conversion to the alcohol and chlorination to give the tetrachlorobutane using conventional functional group transformation chemistry. For example, the acetate can be converted to the alcohol by hydrolysis with a base such as potassium hydroxide and the alcohol may then be transformed into the chloride by reaction with thionyl chloride.

The synthesis of 4,4,4-trichlorobutyl acetate is known using telomerization of allyl acetate with chloroform by the all-in addition of the allyl acetate to the chloroform at the start of the reaction (Macromolecules (1991) 24, 2475–2484). Unfortunately, it was found that even with a large excess of the telogen, chloroform, the reaction gave undesirable high yields of the diadduct (or "bis" product) at the expense of the desired product, 4,4,4-trichlorobutyl acetate. There is therefore a need for an alternative route to the preparation of compounds such as 4,4,4-trichlorobutan-1-ol and 1,4,4,4-tetrachlorobutane.

It was found that the reaction of chloroform with compounds of formula

$CH_2=CH-CH_2-X$ where X is the electron-withdrawing group such as the hydroxy or halide or an ester such as p-toluenesulfonate (tosylate) under the conditions of the process described in the above referenced publication produces little or none of the desired 4,4,4-trichlorobutyl derivative. However, it was found that, contrary to expectation, in the case where X is methanesulfonate (mesylate) the reaction does proceed, and yields the novel corresponding 4,4,4-trichlorobutyl derivative, that is 4,4,4-trichlorobutyl methane sulfonate, and that this compound can be converted readily to the corresponding 4,4,4-trichlorobutanol and thence to the 1,4,4,4-tetrachlorobutane.

Accordingly the present invention provides the novel compound 4,4,4-trichlorobut-1-yl methanesulfonate.

In a further aspect there is provided a process comprising for preparing 4,4,4-trichlorobut-1-yl methane sulfonate which comprises reacting allyl methanesulfonate with chloroform.

The process can be carried out using the all-in addition of the allyl methanesulfonate to the chloroform at the start of the reaction. However in a preferred embodiment of the process the allyl methanesulfonate is added to the chloroform in two or more aliquots. It will be appreciated that the allyl methanesulfonate can be added at either regular or non-regular intervals, and it is not necessary that the same amount of allyl methanesulfonate be added each time. In an extension of this preferred embodiment, the allyl methanesulfonate is continuously fed to the chloroform. This can conveniently be achieved using pump feeding equipment.

Preferably, the overall proportion of allyl methane sulfonate to chloroform is less than one. Preferably the overall proportion of allyl methanesulfonate to chloroform in the range of 1:5 to 1:25, preferably 1:10 to 1:20, for example 1:15.

The reaction is preferably conducted at elevated temperature such as about 100° C. or more, more preferably about 120° C. or more, or about 150° C. or more. The reaction is also preferably carried out at elevated pressure, for example in the range of about 80 psi to about 90 psi. The reaction can conveniently conducted in a pressure reactor.

Many radical initiators are known and any convenient radical initiator may be used in the process. Preferred initiators include organic peroxides such dibenzoyl peroxide or di-t-butyl peroxide and azo compounds such as azobisisobutyronitrile (AIBN). The use of two initiators in combination, for example di-t-butyl peroxide and AIBN, is particularly preferred. All the initiator may be added at the start of the reaction, or it can also be used in an incremental manner.

In addition to its usefulness in the preparation of 4,4,4-trichlorobutanol and 1,4,4,4-tetrachlorobutane as mentioned above, 4,4,4-trichlorobut-1-yl methanesulfonate may be useful in the preparation of compounds of formula:

$$RSCH_2CH_2CH_2CCl_3 \qquad (I)$$

wherein R is an optionally substituted phenyl, an optionally substituted 5- or 6-membered heterocyclic ring, or an optionally substituted benz derivative of a 5- or 6-membered heterocyclic ring, for example by reaction of the corresponding mercapto compound of formula R-SH. The compounds of formula (I) may be converted to compounds of formula

$$RSCH2CH2CH=CF2 \qquad (II)$$

such as, for example, those described in International Patent Applications nos. WO94/06777, WO94/6782 and WO95/24403, which are useful as agricultural pesticides.

The above-mentioned route to the compound of formula (II) has the particular advantage that it reduces the number of synthesis steps compared with the route to the compound of formula (II) via the alcohol and halide.

Various preferred features and embodiments of the present invention will now be described below by way of non-limiting example.

EXAMPLE

This Example illustrates the preparation of 4,4,4-trichlorobutyl methanesulphonate.

(a) Preparation of allyl methanesulphonate (allyl mesylate) The materials and quantities used are set out in the following table:

| Material | Act. Wt. (g) | Strength (%) | MWt | Moles | Mole/Mole |
|---|---|---|---|---|---|
| Allyl alcohol | 20.0 | 98 | 58 | 0.34 | 1.0 |
| Mesyl chloride | 46.9 | 99+ | 114.5 | 0.41 | 1.2 |
| $K_2CO_3$ | 56.5 | 99 | 138 | 0.41 | 1.2 |
| $Me_3N.HCl$ | 3.3 | 98 | 95.6 | 0.03 | 0.1 |
| Ether | 300 cm³ | | | | |

To an agitated solution of distilled allyl alcohol in diethyl ether under a nitrogen atmosphere cooled in ice/water (temperature <5° C.) was added solid potassium carbonate in one portion followed by solid trimethylamine hydrochloride in one portion and the resulting suspension stirred for 5 minutes. Methane sulphonyl chloride (mesyl chloride) was added dropwise to the agitated reaction mixture at 5° C. over a 1 hour period and stirring continued for a further 5 hours at 5° C. after the addition was complete. Water (300 cm$^3$) was added and the mixture vigorously stirred for 15 minutes before separating the two layers and the aqueous layer back extracted twice with diethyl ether (100 cm$^3$). The combined organic layer was dried over anhydrous magnesium sulfate and evaporated under reduced pressure without heating. Final traces of solvent were removed under high vacuum to give allyl methanesulfonate (38.7 g, 83% yield) as a clear colourless oil.

$^1$H nmr (CDCl$_3$): 3.05(s,3H,CH$_3$); 4.75(d,2H,SCH$_2$); 5.40 (m,2H,=CH$_2$) and 6.00 (m, 1H,=CH). MS: 80, 65, 57 and 41.

(b) Preparation of 4,4,4-trichlorobutyl methanesulfonate.

Experiment 1

| Material | Act. Wt. (g) | Strength (%) | MWt | Moles | Mole/Mole |
|---|---|---|---|---|---|
| Allyl mesylate | 7.23 | 94 | 136 | 0.05 | 1 |
| CHCl$_3$ | 92.50 | 99 | 119 | 0.77 | 15 |
| AIBN | 0.25 | 97 | 164 | 1.45 × 10$^{-3}$ | 0.03 |
| (t-BuO)$_2$ | 0.37 | 98 | 146 | 2.45 × 10$^{-3}$ | 0.05 |

Chloroform (67.14 g, 45 cm$^3$), di-t-butyl peroxide (0.073 g) and AIBN (0.049 g) were charged to a 100ml Hasteloy C Parr reactor, purged three times with nitrogen and heated with agitation to 120° C. A solution consisting of allyl methanesulfonate (7.23 g), CHCl$_3$ (25.36 g, 17 cm$^3$), di-t-butyl proxide (0.293 g) and AIBN (0.197 g) was pump fed continuously into the reactor at 120° C. over a 5 hour period. After the addition was complete, the reaction was agitated at 120° C. for a further 1 hour period before cooling to room temperature. Analysis of the composition of crude product by gas chromatography (GC area) indicated that the ratio of unreacted allyl methanesulfonate to the desred product was 0.54:0.46. The reaction mass was concentrated under reduced pressure to give a mixture of recovered starting material (3.98 g) and 4,4,4-trichlorobutyl methane sulfonate (3.86 g, 30% yield).

$^1$H nmr (CDCl$_3$): 2.25(m,2H,CH$_2$); 2.85(m,2H, CH$_2$CCl$_3$); 3.08(s,3H,CH$_3$) and 4.35(t,2H,CH$_2$OMs). MS:159(M-OSO$_2$CH$_3$)$^+$, 123 (M-CH$_2$CCl$_3$)$^+$ and 109 (M-CH$_2$CH$_2$CCl$_3$)$^+$.

Experiment 2

| Material | Act. Wt. (g) | Strength (%) | MWt | Moles | Mole/Mole |
|---|---|---|---|---|---|
| Allyl mesylate | 7.23 | 94 | 136 | 0.05 | 1 |
| CHCl$_3$ | 92.50 | 99 | 119 | 0.77 | 15 |
| AIBN | 0.25 | 97 | 164 | 1.45 × 10$^{-3}$ | 0.03 |
| (t-BuO)$_2$ | 0.37 | 98 | 146 | 2.45 × 10$^{-3}$ | 0.05 |

Chloroform (67.14 g, 45 cm$^3$), di-t-butyl peroxide (0.073 g) and AIBN (0.049 g) were charged to a 100ml Hasteloy C Parr reactor, purged three times with nitrogen and heated with agitation to 150° C. A solution consisting of allyl methanesulfonate (7.23 g), chloroform (25.36 g, 17 cm$^3$), di-t-butyl peroxide (0.293 g) and AIBN (0. 197 g) was pump fed continuously into the reactor at 150° C. over a 5 hour period. After the addition was complete, the reaction was agitated at 150° C. for a further 1 hour period before cooling to room temperature. Analysis by gas chromatography indicated that the composition of crude product contained unreacted allyl mesylate and the desired product in a ratio of 0.59:0.41. The reaction mass was concentrated under reduced pressure to give a mixture of recovered starting material (3.42 g) and desired product (3.21 g, 25% yield).

Experiment 3

| Material | Act. Wt. (g) | Strength (%) | MWt | Moles | Mole/Mole |
|---|---|---|---|---|---|
| Allyl mesylate | 7.23 | 94 | 136 | 0.05 | 1 |
| CHCl$_3$ | 92.50 | 99 | 119 | 0.77 | 15 |
| AIBN | 0.25 | 97 | 164 | 1.45 × 10$^{-3}$ | 0.03 |
| (t-BuO)$_2$ | 0.37 | 98 | 146 | 2.45 × 10$^{-3}$ | 0.05 |

Chloroform (92.50 g, 63cm$^3$), allyl methanesulfonate (7.23 g), di-t-butyl peroxide (0.37 g) and AIBN (0.25 g) were charged to a 100 ml Hasteloy C Parr reactor, purged three times with nitrogen and heated with agitation at 120° C. for 6 hours before cooling to room temperature. Analysis indicated the composition of crude product (GC area) to contain unreacted allyl methane sulfonate and the desired product in a ratio of 0.48:0.52.

We claim:

1. 4,4,4-trichlorobutyl methanesulfonate.

2. A process for the preparation of 4,4,4-trichlorobutyl methane sulfonate which comprises reacting allyl methanesulfonate with chloroform.

3. The process according to claim 2 carried out in the presence of a radical initiator.

4. The process according to claim 3 wherein the radical initiator is selected from organic peroxides and azo compounds.

5. A process according to claim 2, further comprising converting the 4,4,4-trichlorobutyl methanesulfonate to trichlorbutan-1-ol.

6. A process according to claim 2, further comprising converting the 4,4,4-trichlorobutyl methanesulfonate to a compound having the formula

RSCH$_2$CH$_2$CH$_2$CCl$_3$ (I) or RSCH$_2$CH$_2$CH=CF$_2$ (II)

wherein R is selected from the group consisting of optionally substituted phenyl, optionally substituted 5- or 6-membered heterocyclic rings, and optionally substituted benz derivatives of 5- or 6-membered heterocyclic rings.

7. A process according to claim 6 wherein the 4,4,4-trichlorobutyl methanesulfonate is converted to a compound of formula (I) by reaction with a mercaptan having the formula RSH.

* * * * *